(12) United States Patent
Fletcher et al.

(10) Patent No.: US 8,518,384 B2
(45) Date of Patent: Aug. 27, 2013

(54) SPRAY COMPOSITIONS

(75) Inventors: Neil Robert Fletcher, Wirral (GB);
Michael Massaro, Trumbull, CT (US);
Joseph Muscat, Bebington (GB);
Graham Andrew Turner, Wirral (GB)

(73) Assignee: Conopco Inc., Englewood Cliffs, NJ (US)

( * ) Notice: Subject to any disclaimer, the term of this patent is extended or adjusted under 35 U.S.C. 154(b) by 1273 days.

(21) Appl. No.: 11/494,132

(22) Filed: Jul. 27, 2006

(65) Prior Publication Data

US 2007/0036738 A1 Feb. 15, 2007

(51) Int. Cl.
*A61K 8/00* (2006.01)
*A61K 8/18* (2006.01)
*A61Q 15/00* (2006.01)
*A61K 8/28* (2006.01)
*A61K 8/58* (2006.01)

(52) U.S. Cl.
USPC ............................................ 424/65; 424/66

(58) Field of Classification Search
USPC ........................................ 424/65, 401, 489
See application file for complete search history.

(56) References Cited

U.S. PATENT DOCUMENTS

| 4,080,438 | A | * | 3/1978 | Pomot et al. | 424/46 |
|---|---|---|---|---|---|
| 4,680,173 | A | * | 7/1987 | Burger | 424/47 |
| 5,814,309 | A | * | 9/1998 | Panitch | 424/65 |
| 6,099,827 | A | | 8/2000 | Esser | 424/65 |
| 6,387,398 | B1 | * | 5/2002 | Vollhardt et al. | 424/450 |
| 6,485,715 | B1 | * | 11/2002 | Smith et al. | 424/65 |
| 6,649,153 | B1 | | 11/2003 | Parekh et al. | 424/65 |
| 2003/0215399 | A1 | | 11/2003 | Smith et al. | 424/47 |
| 2005/0123494 | A1 | | 6/2005 | Swaile et al. | 424/65 |

FOREIGN PATENT DOCUMENTS

| EP | 957 897 | 11/1999 |
|---|---|---|
| EP | 966 258 | 12/1999 |
| GB | 1 343 653 | 1/1974 |
| GB | 2 062 466 | 5/1981 |
| WO | 98/43604 | 10/1996 |
| WO | 97/48373 | 12/1997 |
| WO | 98/27947 | 7/1998 |
| WO | 2004/014330 | 2/2004 |

OTHER PUBLICATIONS

PCT International Search Report in PCT application PCT/EP2006/006803.

* cited by examiner

*Primary Examiner* — Tracy Vivlemore
*Assistant Examiner* — Genevieve S Alley
(74) *Attorney, Agent, or Firm* — Karen E. Klumas

(57) ABSTRACT

Spray compositions and particularly anhydrous aerosol compositions containing particulate antiperspirant actives exhibit a tendency for nozzle blockage, impeding discharge of the contents when a polyol humectant, such as glycerol, is blended into its base composition. The problem is overcome or at least ameliorated by preparation of a base composition, suitable for employment in conjunction with a propellant, that contains a low molecular weight (liquid) polyethylene glycol (PEG) as humectant, and particularly a PEG of molecular weight 150 to 500.

34 Claims, No Drawings

SPRAY COMPOSITIONS

The present invention relates to spray compositions and in particular to compositions containing an antiperspirant active and a moisturising agent, to their manufacture and to products containing such compositions.

BACKGROUND

Antiperspirant compositions are available using a variety of different applicators, of which one popular choice in some parts of the world is an aerosol, because it avoids physical contact between the applicator and the body. Consequently, aerosol applicators are especially hygienic to operate. An aerosol dispenser comprises a reservoir for a fluid composition that comprises an antiperspirant active and a propellant in fluid communication with a discharge line that is fitted with a valve that is biased to the closed position and terminates in an outlet nozzle having an aperture (spray outlet) through which the composition is sprayed. Typically, such a nozzle aperture (or each of a plurality of nozzle apertures, if employed) has an internal diameter that is significantly smaller than that of the discharge line, and similarly, the passageway through the valve can also have a diameter smaller than that of the rest of the discharge line before the outlet nozzle is reached. The diameter of the outlet nozzle commonly governs the size distribution of droplets, and is often selected so that the user perceives a desirably fine spray of droplets rather than being coarse. It is possible for antiperspirant aerosol compositions to be in the form of an emulsion, but the praiseworthy desire of manufacturers of antiperspirant formulations to eliminate the risk of an aqueous component causing can corrosion of the thin metal wall from which aerosol canisters are typically made, has led them, conventionally, to employ anhydrous compositions commercially in aerosol applicators. In such anhydrous compositions, the antiperspirant active is conventionally in particulate form suspended in a carrier fluid. This is in contrast to when an emulsion with an aqueous phase is employed because astringent antiperspirant salts that act as antiperspirants are water soluble, so that the antiperspirant in emulsions is also in a liquid phase. Accordingly, the problems associated with spraying an emulsion are different from those for an anhydrous formulation.

One of the important parameters of particulate materials for incorporation in compositions dispensed by aerosol canisters is the particle size of such materials. Expressed simply, as particle diameter decreases, there is an increased risk of the particles floating in the air after the aerosol is discharged, thereby increasing the risk of particle inhalation, but on the other hand, as the particle size increases, there is an increased risk of the nozzle aperture becoming wholly or partly blocked and likewise a risk of the passageway through the valve becoming blocked. If either the valve or the spray outlet (nozzle aperture) is blocked, the aerosol effectiveness is impaired if the blockage is only partial, but the impairment is progressively greater to the extreme of being total as the blockage increases. A partial blockage reduces the rate at which the composition can be sprayed, can also reduce the range at which a spray can be applied onto the target body area and furthermore can alter the spray pattern and spray quality. Once a partial blockage arises, there is a significant risk of the blockage worsening, further reducing spray rate, range and quality, ultimately until complete blockage occurs. Accordingly, it is a desideratum of the antiperspirants industry to avoid blockages in aerosol applicators.

During the mid-1990s, research conducted by or on behalf of the Applicants recognised that the employment of astringent antiperspirant salts, be they based on aluminium and/or zirconium (in other words, the very type of salts that are effective at reducing perspiration when topically applied to human skin) tend to cause demoisturisation of the skin and an impairment of skin elasticity. The research team identified that the disadvantage could be ameliorated by the incorporation of a moisturising agent, of which one particularly effective class comprised humectants, including especially humectants that comprise a plurality of hydroxyl substituents. Such compositions are the subjects of EP 910334 (for a variety of applicators) EP957897 (for aerosols) and EP 966258 (for sticks).

In particular, EP 957897 contemplates antiperspirant aerosol compositions containing a polyol humectant such as glycerol. However, it has been found that the incorporation of glycerol (and also propylene glycol) into anhydrous aerosol compositions containing a particulate antiperspirant tends to increase the weighted average particle size (diameter) of the particles in the composition by increasing the fraction of larger particles, possibly by agglomeration of smaller particles. Whilst not being bound by any particular theory, it is surmised that agglomeration is caused or assisted by the presence of the glycerol, possibly acting as a binder of antiperspirant particles. Whatever the cause, the outcome is an increased risk of blockage. Commonly, the problem of blockage increases significantly as the proportion increases of particles having a diameter in excess of 125 microns. At the same time, products containing a significant fraction of particles in the region of 100 microns or higher tend to exhibit poor or impaired sensory properties.

The likelihood of a blend of liquid glycerol and an antiperspirant active causing agglomeration and grit formation is acknowledged in the literature, for example, in U.S. Pat. No. 6,649,153 by Reheis Inc, a commercial producer of astringent antiperspirant actives. That patent specification discloses the problem in the context of producing actives for incorporation in sticks, and advocates the preparation of aluminium-zirconium actives which are complexed with a polyhydroxy compound, all their examples being made using glycerol. The patent does not provide any teaching to discriminate between different polyhydroxy compounds for post-manufacture complexing with aluminium actives. Moreover, the presence of zirconium in the antiperspirant actives, as a practical matter, renders those actives as being unsuitable for use in aerosol compositions, irrespective of whether or not the active is complexed, since zirconium particulates have been banned from incorporation in aerosol-dispensed compositions in many countries, in particular, the USA and EU countries. The instant inventors recognised an inherent and significant disadvantage of a preformed complex. If a material such as a glycerol humectant is complexed with an antiperspirant active, then such material must be released from the complex before it can perform some additional function. Decomplexing is not taught by U.S. Pat. No. 6,649,153.

Whilst for one segment of the antiperspirant market, it is highly desirable to ameliorate skin demoisturisation, it is also desirable to take into account one or more other characteristics that are perceived by the user, such as the roughness of skin to which antiperspirant has been applied, the visibility of fine lines and irritation. The latter is potentially of considerable significance, because this for some users is a governing factor in determining repeat purchase. During the research programme leading to the present invention, the research team has found that one or more of such characteristics can be affected positively by incorporating a glyceride oil, but it would be highly desirable to be able to provide a further improvement.

OBJECTS OF THE PRESENT INVENTION

It is an object of at least some embodiments of the present invention to identify a liquid humectant comprising hydroxyl substituents which can be incorporated in a particulate antiperspirant-containing base composition suitable for incorporation in an anhydrous aerosol composition, which offers a risk of blockage that is less than the risk arising from glycerol.

It will be recognised that aerosol compositions and their manufacture pose different problems from those encountered for contact compositions, such as sticks, by virtue of the need for aerosol compositions to be sprayed compared with, for example the need to solidify stick compositions. Thus, teaching in relation to formulations destined for use as sticks cannot be directly applied to compositions intended to be sprayed.

It is a further object of certain or other embodiments of the present invention to improve or at least ameliorate impairment to skin condition upon application of an antiperspirant composition, including the roughness of the skin and/or appearance of fine lines.

It is a yet further object of various embodiments of the present invention to improve the user perception of skin condition upon application of an antiperspirant composition, including skin irritation.

BRIEF SUMMARY OF THE PRESENT INVENTION

According to a first aspect of the present invention, there is provided an anhydrous base composition suitable for incorporation in an anhydrous aerosol composition for discharge from an aerosol dispenser, said base composition comprising:
(i) a particulate astringent antiperspirant salt;
(ii) an anhydrous carrier fluid for said particulate salt; and
(iii) a humectant,
wherein the humectant comprises a low molecular weight polyethylene glycol that is liquid at 20° C.

Herein, the term low molecular weight in regard to polyethylene glycol is descriptive of any polyethylene glycol that is liquid at 20° C.

In a second aspect of the present invention there is provided an aerosol composition which comprises a composition according to the first aspect together with a propellant.

In a third aspect of the present invention there is provided an aerosol product which comprises a composition according to the second aspect that is housed in an aerosol dispenser.

According to a fourth aspect of the present invention there is provided a process for the manufacture of an aerosol composition in accordance with the second aspect herein above and further in accordance with claim 28 herein.

According to a fifth aspect of the present invention, there is provided a non-therapeutic method for the inhibition of perspiration whilst simultaneously combatting skin demoisturisation by topical application of a composition according to the first aspect.

According to a sixth aspect of the present invention here is provided a non-therapeutic method for reducing skin roughness and/or the appearance of fine lines and/or the perception of irritation whilst simultaneously inhibiting perspiration by the topical application to skin of a composition according to the first aspect.

By the employment of liquid low molecular weight polyethylene glycol as humectant instead of glycerol in base compositions suitable for incorporation in anhydrous antiperspirant aerosol compositions, the risk of blockage of the aerosol dispenser during discharge is averted or at least reduced whilst at the same time retaining the capability of the composition to offset skin demoisturisation arising from the essential employment of an astringent antiperspirant salt. Moreover, by at least minimising and preferably eliminating larger particles in the region of around 100 microns or higher, the sensory properties of the composition are improved relative to glycerol-containing compositions.

Anhydrous herein means that no separate aqueous liquid phase is present. Bound or complexed water, as for example water of hydration in the antiperspirant salt is discounted.

By application of antiperspirant formulations in accordance with the present invention, an improvement in skin condition is observable, for example in skin roughness and/or the presence of fine lines, and/or the user perceives less irritation.

The instant invention provides an anhydrous aerosol composition containing an astringent antiperspirant salt and a bio-available humectant moisturising agent, by which is meant that the moisturising agent is available as soon as or very shortly after the composition comes into contact with skin to impart benefit to the skin. This is in contradistinction to the employment of ingredients in which a polyol has been complexed with the antiperspirant astringent salt.

DETAILED DESCRIPTION OF THE INVENTION AND PREFERRED EMBODIMENTS

The instant invention resides in the selection of a liquid polyethylene glycol as humectant in a base composition suitable for incorporation in an anhydrous humectant-containing antiperspirant aerosol composition.

Antiperspirant aerosol compositions are normally considered to comprise two fractions, a first fraction that is a base composition containing active and optional constituents and a second fraction comprising a propellant. Commonly during manufacture of an aerosol antiperspirant product, the base composition is made by blending together all the composition ingredients other than the propellant, agitating the mixture to suspend the particulate antiperspirant in the carrier liquid, introducing the suspension into the aerosol canister, fitting the outlet delivery line to the canister, sealing the canister and finally pressurising the canister by introduction of the propellant. In an alternative, but related method, an incomplete base composition is blended outside the canister and one or more constituents are introduced into the canister to complete the base formulation.

Base Composition
Particulate Antiperspirant Active

Component (i), the antiperspirant active is a particulate astringent salt and particularly a basic salt such as a basic aluminium salt. It is especially desirable to employ an aluminium chlorohydrate, by which is meant herein a material which satisfies the empirical formula $Al_2(OH)_xCl_y$, in which x+y=6 and y is normally at least 0.5 and commonly not greater than 1.8, the material usually comprising bound water of hydration. The weight proportion of said water of hydration is conventionally not more than 12% and often lies in the range of from 3 to 10%. The term aluminium chlorohydrate herein encompasses materials with specified figures for x and y, such as aluminium sesquichlorohydrate and materials in which the chlorohydrate is present as a complex. It will be recognised that alternative names are sometimes used to indicate the presence of hydroxyl substitution, including aluminium hydroxychloride, aluminium oxychloride or basic aluminium chloride.

Aluminium chlorohydrate as made comprises a mixture of a number of different polymeric species in varying proportions, depending on the molar ratio of aluminium to chloride and the conditions employed during manufacture. All such mixtures are employable herein. It is especially desirable to employ what is commonly called activated aluminium chlorohydrate or enhanced activity aluminium chlorohydrate, sometimes abbreviated to AACH, in which the proportion of the more active species is higher by virtue of its method of manufacture. In one definition of activated, given in EP 6739, the material has greater than 20% Band III. Other methods of making AACH are given in EP 191628 and EP 451395. AACH is often made by recovery of an aluminium chlorohydrate from a dilute solution under strictly controlled reaction/maturing/dewatering/drying conditions. AACH is commercially available by name from suppliers such as Reheis, Summit Research and B K Giulini.

Aluminium chlorohydrate, whether it be activated or not activated, can be complexed, whereupon the CTFA name for the complex is concatenated to aluminium chlorhydrex, followed by the name of the molecule with which it is complexed. Commonly, such complexes include propylene glycol, representative of $C_2$ to $C_6$ glycols and glycine, representative of aminoacids. Any such complexed molecules remain complexed during formation of the invention base and aerosol compositions herein.

The particles of the feedstock aluminium chlorohydrate, be it activated, complexed or otherwise, desirably have a diameter of below 125 microns, preferably $\geq$99% by weight below 100 microns and especially a 95% by weight below 75 microns.

Herein, unless otherwise stated, particle sizes and distributions are those that are obtained by laser light scattering, for example obtained from the appropriate Mastersizer instrument for anhydrous suspensions, obtainable from Malvern Instruments set to produce a volume plot. The instrument is employed with a lens selected in accordance with the maker's instructions to accommodate the expected particle size distribution, (or various lenses can be tested until the best lens is identified) and is preferably operated employing cyclomethicone (DC245™ from Dow Corning) as the liquid dispersant for a sample of the base composition to attain a particles concentration that achieves obscuration, i.e. 10-30% light scattered. Using the Polydisperse analysis model and knowing the dispersant RI, the RI of the particulate material and imaginary RI factor of 0.1, the plot of the particles size (d) distribution and the average particle size D50 is obtained.

For incorporation in many contact applications, the particulate antiperspirant active could alternatively comprise zirconium instead or in addition to aluminium, mutatis mutandis, in the above-given description of aluminium chlorohydrate including complexes with especially glycine, because such actives would enjoy antiperspirant efficacy similar to or greater than that of aluminium chlorohydrate. However, such an option, in practice, is not available to producers of antiperspirant aerosol compositions, because, as noted above, zirconium is banned from incorporation in aerosol compositions in many countries. Accordingly, zirconium is particularly preferably not incorporated into the antiperspirant active used in the subject compositions.

The proportion of antiperspirant salt, eg aluminium chlorohydrate in the base composition is commonly selected in the range of from 5 to 50%, and in many suitable embodiments from 30 to 45% by weight, the weight including any water of hydration and complexed molecules. In other embodiments, for example though not exclusively if a ratio of propellant to base composition of $\leq$1:1 is used, it can be beneficial to incorporate up to 30% of antiperspirant salt, such as from 10 to 30%.

There is a tendency for the particle size distribution of the particulate antiperspirant salt to be altered by blending it with a polyhydric alcohol present in an anhydrous carrier fluid. Advantageously by the selection of a liquid polyethylene glycol and especially of such a polymer of comparatively low molecular weight, the effect on size distribution is markedly less than for glycerol, under conditions that are otherwise the same. It will be recognised that the effect can be controlled by a suitable selection, in combination, of the molecular weight of the polymer and the amount of its incorporation. It is advantageous to control those two parameters together, as well as with the particulate antiperspirant feedstock, such that the resultant base composition contains no more than 0.3% and especially no more than 0.1% of particles and best of all no particles of diameter greater than 125 microns (µm). It is particularly desirable also, to select the polymer and feedstock such that the resultant base composition contains no more than 1% of its particles with a diameter of greater than 100 microns, and most desirably it contains no such particles. It is preferred for the base composition to contain an aluminium chlorohydrate powder, and especially an activated aluminium chlorohydrate powder also having a volume average particle diameter D50 (particle diameter sometimes referred to as particle size) in the region of 15 to 40 microns, and in favoured embodiments of from 20 to 30 microns.

Humectant

The humectant employed herein and usually present in the anhydrous carrier liquid comprises essentially at least one liquid polyethylene glycol (for short PEG). The selection is based on identification by the inventors that such humectants meet simultaneously two criteria. First, they can exhibit moisturisation to an extent that is superior for example to propylene glycol and likewise superior to glycols containing 4 to 6 carbon atoms and secondly they can avoid or at least mitigate the risk of nozzle blockage that can arise when glycerol, an excellent humectant, or propylene glycol, an inferior humectant, is employed. A single oligomer or a mixture of polyethylene glycol oligomers (blend) can be used.

The PEG desirably has a low molecular weight, such as polymers of no more than 20 glycol units, and more desirably the blend has an average molecular weight (conveniently a weight average) of not greater than 820, preferably not greater than 620, and particularly up to 520 and especially up to 420. The PEG polymer blend desirably has an average weight of not less than 150, particularly >150 and in many desirable embodiments of at least 190. PEG polymer blends of a lower molecular weight, compared with a higher molecular weight, tend to be progressively more effective at avoiding antiperspirant active agglomeration, at least until the molecular weight reaches down to around 500 or lower. Accordingly, the proportion of PEG polymer that can be included in the base composition tends to increase with lower molecular weight, for example down to about 500 average, whilst still satisfying desirable particle size constraints.

It is understood that commercially available low molecular weight PEG polymers often comprise a mixture of oligomers. It is especially desirable to employ a polymer (blend) which is free or at least substantially free from the dimer, advantageously less than 5% by weight of the blend, more desirably less than 3% and particularly less than 1%.

Blends can also comprise a small proportion of relatively higher molecular weight oligomers, such as above twice the weight average. It is desirable for the PEG polymer to contain up to 20 glycol units, as indicated hereinbefore, from which the skilled man can deduce that it is desirable to exclude oligomers containing over 20 glycol units. Since in practice polymer blends can contain a small fraction of higher weight oligomers, the blend advantageously contains less than 5% w/w more advantageously less than 3% w/w and most advantageously less than 1% w/w of oligomers containing greater than 20 glycol units.

Advantageously, by the selection of a PEG and particularly a preferred PEG, the producer can produce an antiperspirant aerosol product having perceivable moisturisation employing simple blending techniques and conventionally available aluminium chlorohydrates, including especially activated aluminium chlorohydrates. At the same time, the resultant product does not suffer from problems of agglomeration that can arise if glycerol were to be employed, or at least to a significantly lesser extent. Moreover, the humectant is more readily available to provide skin moisturisation when simply blended into the composition, and as indicated herein, in the liquid carrier, rather than if it were complexed with the antiperspirant active.

Although it may be convenient to incorporate a low proportion of PEG polymer, such as 0.1%, it is preferable to employ a higher proportion and advantageously at least 1% in the base composition. It is preferable to incorporate at least 2% and many attractive compositions contain at least 3% by weight, based on the base composition. Its proportion is normally not more than 10% and in many desirable embodiments is up to 7.5%, and particularly up to 6% by weight of the base composition. In a number of practical embodiments, the maximum proportion of PEG polymer (p %) in the base composition and its average molecular weight (m) are chosen together such that their product p×m is no greater than 2000, and especially when m is at least 400.

The proportion of PEG can, if desired, be chosen in relation to the proportion of antiperspirant active. A convenient weight ratio of antiperspirant active to PEG polymer is selection in the range of 4:1 to 40:1 and often from 7.5:1 to 25:1, and particularly within such ranges when the polymer has an average weight of from 150 or 190 to 420 or 450.

The benefit from blending PEG into the base formulation in comparison with glycerol can be taken in either or both of two ways. In one way, an amount of PEG can be incorporated that is similar to the amount of glycerol that it would have been desired to employ, with the advantage that the agglomeration of the antiperspirant active is insufficient to cause nozzle blocking. In the other way, the relative amount of PEG is increased, though not as far as the proportion at which blocking would become an unacceptable risk.

Furthermore, use of the low molecular weight PEG polymer instead of glycerol not only avoids or reduces the risk of blockage of aerosol discharge lines, but by virtue of reducing or eliminating agglomerates of over 100 microns diameter, the composition retain desirable sensory characteristics, being smooth to the touch.

It is advantageous to substantially avoid incorporating an alternative uncomplexed polyhydric alcohol into the base composition in order avoid at least partly eliminating the benefit obtained by employing a selected PEG polymer. The total proportion of any such alternative polyhydric alcohols should not exceed 1% by weight, preferably not exceed 0.5% and ideally be absent.

Carrier Fluids

The base formulation comprises a carrier fluid or mixture of fluids in which particulate materials are suspended, so that the aerosol expels a pattern of liquid droplets when sprayed. Fluids are liquid at 20° C. It will be recognised that various of the carrier fluids can provide one or more functions in addition to acting as a carrier for particulate materials, for example some act as an emollient, or mask skin deposits to alter the appearance of the composition when applied topically, and/or can mask odour of the composition itself or malodours generated on skin from secretions. For the avoidance of doubt, the term carrier fluid as used herein excludes any liquid polyethylene glycol, though, as indicated hereinbefore, the liquid polyethylene glycol is present in the carrier fluid.

The proportion of carrier fluid(s) in the base composition, including optional or other functional ingredients which are liquid at 20° C., is often at least 35%, and in many base compositions at least 45%, is commonly not higher than 85%, in many embodiments not higher than 75% and in several practical compositions not higher than 65%, % s being by weight of the base composition. In a number of highly desirable formulations the carrier fluid proportion is from 35 to 85% and in other desirable compositions is from 40 to 60%. It is especially desirable for the carrier fluid to comprise at least 90% and particularly at least 95% by weight oils, which is say materials which are liquid at 20° C. and which are water-immiscible.

The carrier fluids employed in the instant invention often desirably comprise one or more volatile silicone oils. By volatile herein is meant having have a measurable vapour pressure at 20 or 25° C. Typically the vapour pressure of a volatile silicone oil lies in a range from 1 or 10 Pa to 2 kPa at 25° C. Volatile silicone oils can be linear or cyclic siloxanes, usually containing from 3 to 9 silicon atoms, and commonly from 4 to 6 silicon atoms, the silicon atoms being substituted by methyl groups, so that their alternative names are methicones and cyclomethicones. It is especially desirable to employ volatile silicone oils in which at least 80% by weight and particularly at least 90% contain at least 5 silicon atoms, such as cyclopentadimethylsiloxane (D5), cyclohexadimethylsiloxane (D6), dodecamethylpentasiloxane and tetradecamethylhexasiloxane. The cylomethicone oils are especially preferred. Such oils are highly desirable for many consumers because they can evaporate without causing undue skin cooling. The volatile silicone oils often comprise at least 30% by weight of the carriers fluids and normally not higher than 95% thereof, and in a number of desirable compositions the weight proportion of the carrier fluids is at least 35%, and particularly at least 40% and in the same or other embodiments of the invention is up to 75%, especially up to 65% and particularly up to 55%.

The carrier oils can alternatively or additionally comprise one or more non-volatile oils, which can be silicone oils and/or non-silicone oils. Preferably, the non-volatile oils are chosen having a refractive index of at least 1.45. Such oils in the base composition can advantageously lessen the appearance of visible residues on skin, only immediately on application but also throughout the period typically from 6 to 24 hours before the antiperspirant composition is washed off.

Non-volatile silicone oils employed herein preferably contain one or more unsaturated substituents such as phenyl or diphenylethyl in replacement of the corresponding number of methyl substituents in polycyclosiloxanes or more preferably in linear siloxanes, often having 2 or 3 silicon atoms. Such non-volatile oils have a higher refractive index than that of the volatile silicone oils and tend to mask the antiperspirant active when it is deposited on skin. The non-volatile oils can also comprise dimethiconols, which as the name suggests are hydroxyl-terminated. The proportion of non-volatile silicone oils in the carrier fluids is commonly from 0 or 0.25 to 10% by weight and often from 0.5 to 5% by weight, such as conveniently in the range of from 1 to 3% by weight of the carrier fluids.

The carrier fluids can alternatively or additionally comprise one or more hydrocarbon fluids, which can be either volatile or non-volatile. Suitable hydrocarbon fluids include liquid aliphatic hydrocarbons such as mineral oils or hydrogenated polyisobutene, desirably selected to exhibit a low viscosity. Further examples of liquid hydrocarbons are polydecene and paraffins and isoparaffins of at least 10 carbon atoms. Hydrocarbon fluids conveniently comprise from 0 to 25% by weight of the carrier fluid.

In at least some advantageous embodiments, the carrier fluids comprise liquid aliphatic or aromatic ester oils. Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. Aliphatic esters include isopropyl myristate, lauryl myristate, isopropyl palmitate, diisopropyl sebacate and diisopropyl adipate. Further and very suitable ester oils include glyceride oils and in particular triglyceride oils derived from glycerol and fatty acids containing at least 6 carbons and especially natural oils.

Suitable liquid aromatic esters include fatty alkyl benzoates. Examples of such esters include suitable $C_8$ to $C_{18}$ alkyl benzoates or mixtures thereof, including in particular $C_{12}$ to $C_{15}$ alkyl benzoates eg those available under the trademark Finsolv. An aryl benzoate, such as benzyl benzoate can also be used. Yet other suitable ester oils includes oils in which a short alkylene group of 1 to 3 carbons, optionally substituted by a methyl group, is interposed between benzene and benzoate residues.

The total proportion of ester oils, including both aliphatic and aromatic ester oils (but excluding any fragrance oil) is often from 0 to 50% by weight of the fluid mixture, is desirably at least 2% and especially is at least 5% by weight. Their total proportion is in many embodiments desirably up to 30% and particularly attractively up to 20% by weight of the fluid mixture. In some especially desirable compositions, the ester oils constitute from 7.5 to 15% of the fluid mixture. The weight ratio of aromatic ester oil to aliphatic ester oil is often selected in the range of from 1:1 to 20:1.

Natural oils which are most desirably employed herein comprise one or more unsaturated C18 fatty acid glycerides. In many instances, the oils comprise one or more triglycerides. The fatty acid residues in the oils can comprise, commonly, from one to three olefinic unsaturated bonds and often one or two. Whilst in many instances the olefinic bonds adopt the trans configuration, in a number of desirable products the bond or bonds adopt the cis configuration. If two or three olefinic unsaturated bonds are present, they can be conjugated. The fatty acid can also be substituted by an hydroxyl group. The natural oils employable herein desirably comprise one or more triglycerides of oleic acid, linoleic acid, linolenic acid or ricinoleic acid. Various isomers of such acids often have common names, including linolenelaidic acid, trans 7-octadecenoic acid, parinaric acid, pinolenic acid punicic acid, petroselenic acid and stearidonic acid. It is especially desirable to employ glycerides derived from oleic acid, linoleic acid or petroselenic acid, or a mixture containing one or more of them.

Natural oils containing one or more of such triglycerides include coriander seed oil for derivatives of petroselinic acid, impatiens balsimina seed oil, parinarium laurinarium kernel fat or sabastiana brasilinensis seed oil for derivatives of cis-parinaric acid, dehydrated castor seed oil, for derivatives of conjugated linoleic acids, borage seed oil and evening primrose oil for derivatives of linoleic and linolenic acids, aquilegia vulgaris oil for columbinic acid and sunflower oil, olive oil or safflower oil for derivatives of oleic acid, often together with linoleic acids. Other suitable oils are obtainable from hemp, which can be processed to derive stearadonic acid derivatives and maize corn oil. An especially convenient natural oil by virtue of its characteristics and availability comprises sunflower oil, ranging from those rich in oleic acid glycerides to those rich in linoleic acid glycerides, rich indicating that its content is higher than that of the other named acid.

The proportion of the natural oil, viz particularly the triglyceride oils of unsaturated fatty acids, in the composition is often selected in the range of from 0.1 to 10% by weight of the carrier mixture, desirably at least 0.25% by weight, especially in the range of from at least 0.5% by weight and in some embodiments particularly in the range of up to 3% by weight and in other embodiments from over 3 to 10% by weight.

Expressed as a proportion of the base composition, in some beneficial embodiments, the triglyceride oil represents from 1 to 8% by weight, and advantageously from 3 to 5% by weight of the base composition. In at least some highly desirable embodiments, it is preferred to employ the triglyceride oil in a weight ratio to the polyethylene glycol humectant in a weight ratio of from 3:1 to 1:3, and conveniently from 3:2 to 2:3. It is especially desirable to employ in such combinations polyethylene glycol having an average (weight average) molecular weight of up to 420. The combination of natural oil and polyethylene glycol demonstrates particularly advantageous skin conditioning properties, including improvement to skin roughness and/or reducing fine lines and is perceived by the user to be less irritating, for example in comparison with similar compositions from which the liquid polyethylene glycol is absent.

A further class of particularly suitable carrier oils comprise non-volatile liquid aliphatic ethers derived from at least one fatty alcohol that desirably contains at least 10 carbon atoms, such as myristyl ether derivatives e.g. PPG-3 myristyl ether or lower alkyl ($\leq C_6$) ethers of polygylcols (preferably polypropylene glycol and especially 10 to 20 units, such as an ether named as PPG-14 butyl ether in the CTFA. It is often convenient for the aliphatic ether to constitute at least 10%, and especially at least 15%, particularly up to 50% and very desirably up to 35% % s by weight of the carrier mixture. Such ethers, and especially those having a refractive index of above 1.46 can assist in masking the visibility of deposits on the skin, thereby complementing the positive skin conditioning properties of the overall composition. It can be very desirable to select the ether in a weight ratio to the antiperspirant active of at least 0.3:1 such as up to 0.8:1, one practical range being from 0.5:1 to 0.7:1.

It is often convenient to select the aromatic ester oil and non-volatile aliphatic ether to volatile silicone oil in a weight ratio of from 2:3 to 1:5, and especially from 1:2 to 1:3.

A further class of carrier fluids can be employed herein comprises water-immiscible aliphatic alcohols, and particularly those having a boiling point of higher than 100° C. These include branched chain alcohols of at least 10 carbon atoms and in many instances up to 30 carbon atoms, particularly 15 to 25, such as isostearyl alcohol, hexyl-decanol and octyl-dodecanol. It will be recognised that octyl dodecanol is an especially favoured water-immiscible aliphatic alcohol in the instant compositions, because it not only acts as an emollient oil but additionally moisturises skin by the mechanism of occlusion. Other suitable water-immiscible alcohols include intermediate chain length linear alcohols, commonly containing from 9 to 13 carbon atoms, such as decanol or dodecanol. Such alcohols can often constitute at least 0.1% and particularly at leas 0.5% by weight of the carrier mixture, in many compositions being not more than 5% and particularly up to 3% by weight of the mixture.

The instant compositions preferably contain a fragrance oil normally at least 10 and often at least 20 fragrance constituents, some of which are sometimes extracted from flora or fauna and others of which are synthesised that are blended together to produce a perfume that is pleasing to the user of the composition. Such a fragrance oil is normally a complex mixture of chemical classes and accordingly, its proportion is excluded from calculations of the proportion of the other constituents of the carrier mixture, including specifically ester, ether and alcohol classes. The proportion of fragrance oil in the carrier mixture is at the discretion of the antiperspirant composition manufacturer, it normally being selected in the range of from 0 to 15% by weight of the mixture, often constituting not more than 10% by weight and especially at least 3% by weight.

In a number of preferred embodiments, the anhydrous compositions herein are preferably at least substantially free from water-miscible monohydric alcohols, that is to say the base composition contains less than 10%, particularly less than 5%, especially less than 3% and more particularly less than 1% of such an alcohol, for example an aliphatic monohydric alcohol containing up to 6 carbons such as ethanol and/or propanol, and most particularly contains none at all.

Similarly, in the same or other embodiments, desirable compositions are at least substantially free, virtually completely free, from a dihydric alcohol other than low molecular weight polyethylene glycol, such that for example the total content of dihydric alcohol in the base composition including the essential polyethylene glycol is not greater than 1% by weight, and the content of propylene glycol and related C3 to C6 glycols is advantageously none at all, % s being herein by weight. By at least almost complete avoidance of such glycols, the deleterious effects of including them are at least lessened or in the extreme avoided.

The carrier fluid for the particulate antiperspirant salt in the presence of the polyethylene glycol preferably is a mixture of at least three oils that are liquid at 20° C., of which, highly desirably, at least one is a volatile oil, particularly a volatile silicone oil, at least one is a non-volatile oil such as a dimethicone oil and/or an ether oil and/or especially a triglyceride oil of a C18 aliphatic acid. The weight ratio of volatile to non-volatile oils is desirably from 2:1 to 1:3, and particularly from 1:1 to 1:2.

Additional Ingredients

It is desirable for aerosol antiperspirant compositions to contain a suspending aid. Suitable suspending agents include colloidal silicas, suitably pyrogenic, and clays such as montmorillonite clays such as bentonites and hectorites, and particularly suspending aids having hydrophobically treated surfaces. A particularly preferred bentonite is hydrophobic bentonite, e.g. aids which are commercially available under the trade mark Bentone, eg Bentone LT, Bentone 14, Bentone 27, Bentone 34, and Bentone 38/38V and is a bentonite treated with hydrophobic cationic materials. Other suitable clay suspending aids include colloidal magnesium aluminum silicates. Advantageously, the suspending aid is utilised at a level of from at least 1%, and preferably at least 2% by weight of the base composition, often at up to 8% and in some desirable embodiments at up to 6%. It is often beneficial to calculate the proportion of suspending aid by reference to the antiperspirant active, and in particular in a weight ratio of antiperspirant active:suspending aid of from 3:1 to 6:1.

It can be advantageous to employ an activator in conjunction with a clay suspending aid, for example to encourage variations in the manufacturing process from the base formulation. Clay activators include ethanol and especially propylene carbonate. The amount of activator is preferably selected in the range of from 25 to 75% of the weight of the suspending aid, is advantageously at least 35% and is often not more than 60%.

The instant compositions can include one or more additional optional constituents which have hither to been incorporated or proposed for incorporation in antiperspirant compositions. Such optional constituents may be liquid (in which event there form part of the carrier mixture) or solid, and normally comprise in total not more than 10% and often not more than 5% by weight of the base composition. Such optional constituents can comprise non-antiperspirant deodorant actives, such as antimicrobial actives such as polyhexamethylene biguanides, e.g. those available under the trade name Cosmocil™ or chlorinated aromatics, eg triclosan available under the trade name Irgasan™, non-microbiocidal deodorant actives such as triethylcitrate, bactericides and bacteriostats. Yet other deodorant actives can include zinc salts such as zinc ricinoleate. The compositions can additionally or alternatively contain as bacteristat an iron chelator such as pentenoic acid which hinders bacterial growth/reproduction. The proportion of the deodorant active in the base composition is often selected in the range of from about 0.05 to 2% by weight of the base composition and especially from 0.1 to 0.5%.

Yet other optional ingredients can include sensory modifiers, such as talc or finely divided polyethylene, such as in an amount of up to 3% by weight; colourants, for example in a proportion of up to 0.5% of the base compositor; skin cooling agents such as menthol often selected in an amount of up 0.5%, particularly up to 0.2% of the base compositions and wash-off agents such as non-ionic surfactants, and particularly polyethoxylated fatty alcohols or acids, for example in an amount of up to about 3% of the base composition.

Aerosol Compositions

Propellant

The anhydrous aerosol composition according to the second aspect of the present invention comprises a propellant in addition to the base composition described herein above. Commonly, the propellant is employed in a weight ratio to the base composition of from 95:5 to 5:95, the weight proportion chosen depending in practice on the choice of propellants, the internal pressure which the manufacturer seeks to generate and the architecture of the aerosol canister. Depending on the propellant, in such aerosol compositions the ratio of propellant to base composition is normally at least than 20:80, generally at least 30:70, particularly at least 40:60, and in many formulations, the weight ratio is from 90:10 to 50:50 within which a ratio range of from 70:30 to 90:10 is sometimes preferred. Particularly suitable ratios are in the regions of 3:1, 4:1 or 7:1, for example the propellant proportion of the total composition being within ±1% or 1.5% of 75%, 80% or 87.5% respectively.

Propellants herein generally accord with one of three classes; i) low boiling point gasses liquifided by compression, ii) volatile ethers and iii) compressed non-oxidising gases.

Class i) is conveniently a low boiling point material, typically boiling below −5° C., and often below −15° C., and in particular, alkanes and/or halogenated hydrocarbons. Examples of suitable alkanes include particularly propane, butane or isobutane, often in varying admixtures of the three components, possibly containing a fraction of pentane or isopentane. Examples of halogenated hydrocarbons are fluorocarbons and chlorofluorocarbons such as, for example, 1,1-difluoroethane, 1-trifluoro-2-fluoroethane, dichlorodifluoromethane, 1-chloro-1,1-difluoroethane, and 1,1-dichloro-1,1,2,2-tetrafluoroethane. It is particularly desirable to employ the first class of propellant. Such propellants are commonly employed at a weight ratio to the base composition of from 1:2 and especially at least 1:1 up to 95:5.

The second class of propellant comprises a very volatile ether of which the most widely employed ether hitherto is dimethyl ether. This propellant can advantageously be employed at relatively low weight ratio of propellant to base composition, for example to as low as 5:95. It can also be employed in admixture with, for example compressible alkane gasses.

The third class of propellant comprises compressed non-oxidising gasses, and in particular carbon dioxide or nitrogen. Inert gases like neon are a theoretical alternative.

Aerosol Product Manufacture

An aerosol product according to the present invention can be made conveniently by first blending together the ingredients of the base composition in a vessel, less any ingredient intended to be added later, agitating the mixture to suspend the particulate antiperspirant active, charging an aerosol canister with the mixed base composition and separately charging any other ingredient not blended previously into the base composition, charging either before, after or simultaneously, fitting and sealing the discharge line containing the valve onto the aerosol canister and injecting propellant gas into the canister through the discharge line.

The selection of the aerosol canister is at the discretion of the manufacturer of the aerosol product. Conveniently, the canister itself can be made from tin plate or aluminium. The discharge line includes a valve biased to the closed position, and may be depressed or tilt valve. The valve can be opened by depression or lateral movement as is determined by the valve of an actuator. The discharge line terminates in a spray nozzle which in conventional aerosol dispensers is moulded with the spray nozzle to form a depressor button or which in more recent developments such as in EP 1040055 or EP 1255682 comprises rotational or lateral relative motion of elements to prevent the valve being opened prematurely. The nozzle outlet has an internal diameter that is usually selected within the range of from 300 to 800 microns, particularly not greater than 600 microns and in many embodiments from 350 to 450 microns. This is particularly beneficial in that it enables the composition to be sprayed without an undue risk of blockage through nozzles of similar internal diameter currently employable with corresponding otherwise similar compositions that lack the humectant moisturiser. This of course has the added advantage of allowing the canister to deliver a similar spray pattern, if desired, at a similar pressure to that of the humectant-free composition.

Topical Application

The base composition of the instant invention can be sprayed onto skin, and particularly into the underarm (axilla) in a conventional manner for spraying liquid compositions. Very conveniently, the base composition can be mixed with a propellant prior to being sprayed from an aerosol canister. The canister is desirably held at a distance of between 12 and 18 cms from the armpit and the valve in the discharge line opened. The composition can be sprayed at the discretion of the user for a conventional period of time, such as from about 2 to 5 seconds per armpit.

Having described the invention, as well as preferred embodiments thereof, in general terms, particular embodiments thereof will described in more detail hereinafter by way of example only.

In the Examples and comparisons (designated by the prefix C), the ingredients employed are summarised in Table 1 below in which ™ indicates a trade mark of the supplier:—

TABLE 1

| Ingredient/Trade Name | INCI Name | Supplier |
|---|---|---|
| Carrier Fluids | | |
| CF1/DC245 ™ | Cyclomethicone | Dow Corning |
| CF2/DC1501 ™ | Dimethiconol | Dow Corning |
| CF3/Fluid AP ™ | PPG-14 Butyl Ether | Amerchol |
| CF4/Eutanol G ™ | Octyl dodecanol | Henkel |
| CF5/Agripure 80 ™ | *Helianthis Annuus* | Cargill plc |
| CF6/Fragrance | Fragrance | |
| Solid Ingredients | | |
| Aid/Bentone 38V ™ | Disteardimonium Hectorite | Elementis |
| AACH/AACH 7172 ™ | Activated Aluminium Chlorohydrate Powder | Summit |
| Humectant | | |
| PEG4/Polyglykol 200USP ™ | PEG-4 | Clariant |
| PEG-4b/Carbowax PEG200E | PEG-4 | Dow Chemicals |
| PEG8/Polyglykol 400 ™ | PEG-8 | Clariant |
| PEG12/Polyglykol 600 ™ | PEG-12 | Clariant |
| PEG40/Polyethylene Glycol 2000 ™ | PEG-40 | Sigma |
| 3ol/Pricerine 9091 ™ | Glycerin | Uniqema |
| Preservative | | |
| BHT/Tenox BHT | BHT | Eastman Chemicals |

The base compositions of the Examples and comparisons were made by charging a vessel with the liquid ingredients and then the solid ingredients in the amounts specified in Table 2 below and agitating the resulting mixture with a laboratory stirrer until the antiperspirant active was suspended. For certain compositions, a sample was withdrawn for analysis.

Subsequently, the base composition is introduced into an aluminium aerosol canister, a conventional valved discharge line is fitted having an outlet nozzle of 0.4 mm, sealed and pressurised by injection of a hydrocarbon propellant (propane, butane and iso-butane (CAP-40™, ex Calor) in a weight ratio of propellant to base composition of 3:1.

TABLE 2

| | Ex 1 | Ex 2 | Ex 3 | Ex 4 | Ex 5 | Ex 6 | C 1 | C 2 | C3 |
|---|---|---|---|---|---|---|---|---|---|
| | | | | | parts by weight | | | | |
| CF1 | 19.13 | 19.13 | 19.13 | 21.13 | 21.13 | 21.13 | 19.13 | 21.13 | 19.13 |
| CF2 | 1.54 | 1.54 | 1.54 | 1.54 | 1.54 | 1.54 | 1.54 | 1.54 | 1.54 |
| CF3 | 22.36 | 22.36 | 22.36 | 22.36 | 22.36 | 22.36 | 22.36 | 22.36 | 22.36 |
| CF4 | 0.9 | 0.9 | 0.9 | 0.9 | 0.9 | 0.9 | 0.9 | 0.9 | 0.9 |
| CF5 | 4 | 4 | 4 | 4 | 4 | 4 | 4 | 4 | 4 |

TABLE 2-continued

|       |       |       |       |       |       |       |       |       |       |
|-------|-------|-------|-------|-------|-------|-------|-------|-------|-------|
| CF6   | 5.38  | 5.38  | 5.38  | 5.38  | 5.38  | 5.38  | 5.38  | 5.38  | 5.38  |
| AACH  | 38.46 | 38.46 | 38.46 | 38.46 | 38.46 | 38.46 | 38.46 | 38.46 | 38.46 |
| Aid   | 4.23  | 4.23  | 4.23  | 4.23  | 4.23  | 4.23  | 4.23  | 4.23  | 4.23  |
| PEG4  | 4     |       |       | 2     |       |       |       |       |       |
| PEG8  |       | 4     |       |       | 2     |       |       |       |       |
| PEG12 |       |       | 4     |       |       | 2     |       |       |       |
| PEG40 |       |       |       |       |       |       |       |       | 4     |
| 3ol   |       |       |       |       |       |       | 4     | 2     |       |

|       |       | Ex 7  | Ex 8  | Ex 9  | Ex 10 | Ex 11 | Ex 12 | Ex 13 | Ex 14 | Ex 15 |
|-------|-------|-------|-------|-------|-------|-------|-------|-------|-------|-------|
|       |       |       |       |       | parts by weight |  |  |  |  |  |
| CF1   |       | 23.13 | 21.13 | 23.13 | 23.13 | 25.13 | 23.13 | 23.12 | 23.12 | 23.12 |
| CF2   |       | 1.54  | 1.54  | 1.54  | 1.54  | 1.54  | 1.54  | 1.54  | 1.54  | 1.54  |
| CF3   |       | 22.36 | 22.36 | 22.36 | 22.36 | 22.36 | 22.36 | 22.36 | 22.36 | 22.36 |
| CF4   |       | 0.9   | 0.9   | 0.9   | 0.9   | 0.9   | 0.9   | 0.9   | 0.9   | 0.9   |
| CF5   |       | 0     | 2     | 0     | 2     | 0     | 2     | 4     | 4     | 4     |
| CF6   |       | 5.38  | 5.38  | 5.38  | 5.38  | 5.38  | 5.38  | 5.38  | 5.38  | 5.38  |
| AACH  |       | 38.46 | 38.46 | 38.46 | 38.46 | 38.46 | 38.46 | 38.46 | 38.46 | 38.46 |
| Aid   |       | 4.23  | 4.23  | 4.23  | 4.23  | 4.23  | 4.23  | 4.23  | 4.23  | 4.23  |
| PEG4  |       | 4     |       |       | 2     |       |       | 0.011 |       |       |
| PEG8  |       |       | 4     |       |       | 2     |       |       | 0.011 |       |
| PEG12 |       |       |       | 4     |       |       | 2     |       |       | 0.011 |

The particle size distribution of solids included within the composition were measured at laboratory ambient temperature (approximately 23° C.) using a Malvern Mastersizer X for the formulations specified in Table 3 below. The instrument employed 100 mm range lens a beam length of 2.4 mm, a Presentation setting of 2NHE, analysis model of Polydisperse, Volume distribution type, and employed cyclomethicone (DC245) as dispersant. The Dispersant RI was 1.396, the particles RI was 1.5330 and the imaginary RI 0.1. The sample was diluted with dispersant until obscuration point was reached (in the range of 10-30% laser light scattering). The test was then continued until sufficient number of particles had been detected and the size distribution of particles of diameter d and average by volume (D50) was calculated.

TABLE 3

Particle size distribution

|         |             | Ex 1  | Ex 2  | Ex 3  | C1    | C3    |
|---------|-------------|-------|-------|-------|-------|-------|
| D50     | microns     | 22.98 | 26.59 | 47.37 | 42.18 | 25.25 |
| d < 2.23| % by volume | 11.35 | 7.65  | 4.24  | 6.11  | 0     |
| d < 10.27| % by volume| 23.63 | 18.18 | 10.28 | 10.49 | 0     |
| d > 100 | % by volume | 0     | 0     | 3.11  | 5.49  | 6.83  |
| d > 125 | % by volume | 0     | 0     | 0.27  | 1.52  | 5.63  |

From Table 3, it can be seen that compositions of Examples 1 and 2 were fully acceptable and preferable as regards their particle size distribution in that none of their particles exceeded 100 microns diameter. Not only do such compositions have a significantly reduced risk of causing blockage of spray outlets, but they also demonstrate superior sensory properties in comparison with the composition of comparisons C1 and C3. The composition of Example 3 was closer towards the margin of acceptability, in that a very small proportion of particles exceeded 125 microns diameter and also a small fraction of particles were greater than 100 microns. The composition of Example 3 can be modified so that the proportion of particles exceeding 125 microns is reduced, preferably to zero, by a sufficient reduction in the proportion of PEG 600 in the composition and/or by a reduction in the average molecular weight of the low molecular weight polyethylene glycol incorporated, i.e. by increasing the relative proportion of PEG 400 and/or PEG 450 or PEG 500 compared with PEG 600. By comparison, when a higher molecular weight PEG was employed, which was of waxy consistency, as in Comparison C3, a very significant proportion of the particles had a diameter of above 125 microns, even though the average particle size (D50) would have been acceptable.

Humectancy Test

In this test, the extent to which skin hydration was improved was measured for three formulations. F1 (control) comprised an aerosol base composition containing 4% by weight Helianthis Annuus as a reference control, F2 a composition which additionally contained 4% by weight PEG-400 (substituted for a like amount of cyclomethicone), but otherwise identical to F1, and F3 (comparison) which additionally contained 4% by weight glycerol (substituted for a like amount of cyclomethicone), but otherwise identical to F1.

16 subjects participated in the study. Subjects applied 0.05 g of each test product on a separate 9 $cm^2$ site on the volar forearm twice a day for two days and once on the morning of the third day. 5 hours after the final application of product, stratum corneum hydration was measured using a Corneometer CM-825® (Courage & Khazaka GmbH, Cologne, Germany). The data obtained are summarised in Table 4 below. Statistical analysis was performed using Student's t-test.

TABLE 4

3-day humectancy study results

| Formulation  | Hydration (au) ± SD |
|--------------|---------------------|
| F1 (control) | 31 ± 6              |
| F2           | 34 ± 8              |
| F3           | 34 ± 6              |

From Table 4, it can be seen that the extent of hydration achieved in F2 with PEG-400 (Polyglykol 400) (p=0.05) in accordance with the invention was similar to that achieved in F3 with glycerol.

1. 5-Day Elasticity Study

In this study, the improvement in skin elasticity obtained by incorporating a PEG polymer according to the present invention was measured by comparing F1 with a composition F4 employing 4% Polyglykol 200 instead of Polyglykol 400.

31 subjects participated in this study. Subjects applied 0.2 g of each test product on a separate 20 cm² site on the volar forearm twice a day for four days and once on the morning of the fifth day. Five hours subsequent to the final application of product, skin elasticity was measured using the Dermal Torque Meter™ (Dia-Stron Ltd, Andover, UK). The data obtained are summarised in Table 5 below. Statistical analysis was performed using Student's t-test.

TABLE 5

5-day DTM Study

| Formulation | Elasticity (Fitted elastic constant) ± SD |
|---|---|
| F1 (control) | 0.776 ± 0.119 |
| F4 | 0.845 ± 0.159 |

From Table 5, it can be seen that the incorporation of a PEG polymer according to the present invention in F4 significantly improved the elasticity of the skin, p=0.04, confirming that effective moisturisation had occurred.

Example 16

In this Example, the skin conditioning of a composition according to the present invention was compared with that from a control composition lacking polyethylene glycol.

The compositions are summarised in Table 6 below:—

TABLE 6

| Ingredient | Example 16 By weight | Control By weight |
|---|---|---|
| AACH | 5.00 | 5.00 |
| Aid | 0.55 | 0.55 |
| CF1 | 2.503 | 3.023 |
| CF2 | 0.20 | 0.20 |
| CF3 | 2.907 | 2.907 |
| CF5 | 0.52 | 0.52 |
| PEG-4b | 0.52 | 0 |
| Fragrance | 0.70 | 0.70 |
| BHT | 0.10 | 0.10 |
| CAP-40 | 87.00 | 87.00 |

Skin Irritation, Roughness and Lines

The evaluations were conducted on 30 female panellists.

The test procedure lasted 5 weeks, of which the first week represented a provocation phase and the subsequent four weeks a recovery phase. Throughout the test panellists were requested to shave their underarms on each Wednesday and Saturday evenings, solely using disposable razors after application of a wetted mild soap bar and thereafter rinsing with water.

In the provocation phase, the panellists applied four times daily under both arms an antiperspirant stick having the following composition:—

TABLE 7

| Ingredient | % by weight |
|---|---|
| 12-hydroxy stearic acid | 7.00 |
| N-lauroyl glutamic acid di-n-butyl amide | 2.00 |
| Cyclomethicone DC245 | 46.90 |
| Octyl dodecanol | 14.00 |
| AZAG Reach 908 | 26.0 |
| $C_{20-40}$ Pareth 40 | 2.50 |
| $C_{20-40}$ Alcohol | 0.50 |
| NA EDTA | 0.10 |
| Fragrance | 1.00 |

During the subsequent recovery phase, each panellist applied one product four times daily under the left arm and a second product four times daily under the right arm, the allocation being randomised between panellists to achieve a balance of left and right arm application for the example and control products. The aerosol cans were weighed weekly to confirm that panellists were applying consistent amounts to each arm. The skin condition of the panellists was assessed on Monday, Wednesday and Friday of each week.

The irritation suffered by the panellists was assessed by a trained analyst against a 5 point scale, in which 1 represents very mild irritation, (redness), increasing progressively to 5 representing severe irritation (erythma etc). The assessed scores for each product were averaged and are given in Table 8 below.

| Assessment | | |
|---|---|---|
| Assessment (Days into Recovery Phase) | Control | Example |
| 0 | 1.37 | 1.46 |
| 3 | 1.15 | 1.14 |
| 6 | 0.94 | 0.90 |
| 8 | 1.21 | 1.04 |
| 10 | 1.32 | 1.12 |
| 13 | 1.16 | 0.94 |
| 15 | 1.10 | 0.74 |
| 17 | 1.14 | 0.76 |
| 20 | 0.96 | 0.78 |
| 22 | 1.00 | 0.82 |
| 24 | 1.15 | 0.88 |
| 27 | 0.85 | 0.74 |
| 29 | 1.04 | 0.84 |

From Table 8, it can be seen that the Example product consistently reduced irritation relative to the control product, which differed by lacking the PEG-4. A statistical evaluation of the data indicated that the difference was significant at the 95% confidence level from day 10 onwards.

The roughness and presence of lines in the skin were measured using Phaseshift Rapid In Vivo Measurement of Skin (PRIMOS) (digital fringe projection with micromirror display devices) on replicas of axillary skin of each panellist, (made using Silflo™ and the average across the panellists, recorded. The measurement was conducted under using the high resolution PRIMOS apparatus (lateral 26 μm and vertical 2 μm) from G F Messtechnik GmbH. The apparatus projects stripes (fringes) with known sinusoidal brightness intensity onto the surface being measured. The lines and rough elements-distort the pattern, and the resultant distortion is recorded at a set triangulation angle by a CCD camera. The topography of the surface is calculated from the position of the distorted stripes and the grey value of registered image points, using the program provided with the apparatus. This provides numbers for the overall roughness of the surface and the extent of fine lines. The difference between those measurements at days 0 and 29 was recorded in Table 9 below.

TABLE 9

|  | Control | Example |
|---|---|---|
| Roughness reduction | | |
| Mean CFB | 1.8 | 5.5 |
| Fine line improvement | | |
| Mean CFB | 6.7 | 18.2 |

From Table 9, it can be seen that the Example product reduced the roughness of the skin substantially more than did the control product and likewise there was a substantial improvement in the appearance of fine lines for the example compared with the control. This demonstrates that the use of the Example product "repairs" the skin after challenge (such as by shaving) noticeably better than did the control product.

The invention claimed is:

1. An anhydrous base composition suitable for incorporation in an anhydrous aerosol composition intended for discharge from an aerosol dispenser, said base composition comprising:
   (i) a particulate astringent antiperspirant salt;
   (ii) an anhydrous carrier fluid for said particulate salt; and
   (iii) a humectant,
wherein the humectant comprises a low molecular weight polyethylene glycol that is liquid at 20° C., said low molecular weight polyethylene glycol being present in an amount of from 1% to 10% by weight of the base composition and said anhydrous carrier fluid being present in an amount of from 35% to 85% by weight of the base composition, and wherein if a water-miscible monohydric alcohol is present, it is present in an amount less than 3% by weight of the base composition, and wherein the polyethylene glycol has an average molecular weight of up to 520, and wherein the base composition contains not more than 0.3% by volume of particles having a diameter of greater than 125 microns.

2. A composition according to claim 1 in which the composition contains not more than 1% by volume of particles having a diameter of greater than 100 microns.

3. A composition according to claim 2 in which the composition is free from particles having a diameter of greater than 100 microns.

4. A composition according to claim 1 in which the polyethylene glycol has an average molecular weight of not less than 150.

5. A composition according to claim 4 in which the polyethylene glycol has an average molecular weight of from 190 to 420.

6. A composition according to claim 1 which is substantially free from ethylene glycol dimer.

7. A composition according to claim 1 in which the polyethylene glycol is present in a weight ratio to the particulate antiperspirant salt of 1:4 to 1:40.

8. A composition according to claim 7 in which the polyethylene glycol is present in a weight ratio to the particulate antiperspirant salt of from 1:25 to 1:6.

9. A composition according to claim 1 which comprises by weight
   from 10 to 50% of (i)
   from 35 to 85% of (ii)
   from 1 to 6% of (iii) and
   from 0 to 10% of a fragrance, and
   wherein the base composition is substantially free from dihydric alcohol other than the low molecular weight polyethylene glycol.

10. A composition according to claim 9 which comprises by weight from 30 to 45% of (i) and from 40 to 60% of (ii).

11. A composition according to claim 1 in which the carrier fluid comprises a volatile silicone oil, optionally together with a non-volatile oil which is a silicone oil and/or a non-silicone oil.

12. A composition according to claim 11 in which the weight proportion of non-volatile oil is from 15 to 45% of the base composition.

13. A composition according to claim 11 in which the weight proportion of volatile silicone oil is from 15 to 45% of the base composition.

14. A composition according to claim 11 in which the volatile silicone oil and the non-volatile oil are present in a weight ratio in the range of from 5:1 to 1:2.

15. A composition according to claim 14 in which the volatile silicone oil and the non-volatile oil are present in a weight ratio in the range of from 3:2 to 2:3.

16. A composition according to claim 11 in which the non-volatile oil comprises one or more oils selected from aliphatic ether oils, aromatic ester oils and aryl-substituted silicone oils having a refractive index of at least 1.45.

17. A composition according to claim 11 in which the non-volatile oil comprises from 0.25 to 2.5% by weight based on the base composition of a water-immiscible branched aliphatic alcohol containing from 12 to 30 carbon atoms.

18. A composition according to claim 11 in which the non-volatile oil comprises from 0.25 to 6% by weight of a triglyceride ester oil.

19. A composition according to claim 1 in which the base composition further comprises a suspension aid.

20. A composition according to claim 19 in which the suspension aid is a particulate clay.

21. A composition according to claim 20 in which the particulate clay is a hydrophobic clay.

22. A composition according to claim 19 in which the suspension aid is present in a weight ratio to the antiperspirant salt of from 1:87 to 1:13.

23. An anhydrous aerosol composition which comprises a base composition according to claim 1 together with a propellant.

24. An aerosol composition according to claim 23 in which the weight ratio of base composition to propellant is selected in the range of from 20:80 to 5:95.

25. An aerosol composition according to claim 24 in which weight ratio of base composition to propellant is selected in the range of from 30:70 to 10:90.

26. A process for making an anhydrous antiperspirant aerosol composition containing a moisturising agent which comprises the steps of:
   i) forming a mixture of a particulate astringent antiperspirant salt, an anhydrous carrier fluid for said particulate salt and a humectant as described in claim 1,
   ii) agitating the mixture to distribute the particulate salt in the carrier fluid,
   iii) simultaneously or sequentially with step ii) introducing the mixture into a dispensing container
   iv) and after steps ii) and iii) introducing propellant into the dispensing container.

27. An aerosol product comprising an anhydrous aerosol composition as described in claim 23, housed in an aerosol dispenser having a nozzle aperture of diameter from 300 to 800 microns and preferably from 350 to 450 microns.

28. A non-therapeutic method of simultaneously inhibiting perspiration and ameliorating or preventing skin demoisturisation comprising topically applying to skin a composition as described in claim 1.

29. A composition according to claim 1 wherein if a water miscible monohydric alcohol is present, it is present in an amount less than 1% by weight of the base composition.

30. A composition according to claim 1 wherein the carrier fluid comprises at least 90% by weight of materials which are liquid at 20° C. and which are water-immiscible.

31. A composition according to claim 1 wherein the carrier fluid comprises at least 95% by weight of materials which are liquid at 20° C. and which are water-immiscible.

32. A composition according to claim 11 in which the proportion of non-volatile oil is from 18 to 35% of the base composition.

33. A composition according to claim 11 in which the proportion of non-volatile oil is from 18 to 30% of the base composition.

34. A composition according to claim 1 in which the base composition is free of particles having a diameter of greater than 125 microns.

\* \* \* \* \*